United States Patent
Chiang

(10) Patent No.: US 6,851,150 B2
(45) Date of Patent: Feb. 8, 2005

(54) BLOCK HEAD STRUCTURE OF ELECTRIC TOOTHBRUSH

(76) Inventor: Cheng-Chieh Chiang, 10F-10, No. 28, Chung-Ho St., Pae-Tou District, Taipei (TW)

( * ) Notice: Subject to any disclaimer, the term of this patent is extended or adjusted under 35 U.S.C. 154(b) by 103 days.

(21) Appl. No.: 10/321,489

(22) Filed: Dec. 18, 2002

(65) Prior Publication Data

US 2004/0010872 A1 Jan. 22, 2004

(30) Foreign Application Priority Data

Jul. 22, 2002 (TW) .......................................... 9121147 U

(51) Int. Cl.[7] .............................................. A46B 13/02

(52) U.S. Cl. .............................. 15/28; 15/22.1; 15/22.2

(58) Field of Search ................................ 15/22.1, 22.2, 15/23, 28

(56) References Cited

U.S. PATENT DOCUMENTS 5,213,434 A * 5/1993 Hahn .......................... 403/59
6,367,108 B1 * 4/2002 Fritsch et al. .................. 15/28

* cited by examiner

Primary Examiner—Randall Chin
(74) Attorney, Agent, or Firm—Bacon & Thomas

(57) ABSTRACT

A block head structure for an electric toothbrush. The structure can be slipped over and connected to a driving end on the block handle of an electric toothbrush of different style. The structure includes a block head sleeve, a set of bristles, a driving axle bush and a connecting portion. The driving axle bush has an excavated section corresponding to the position of the driving axle. A bridge-like member is provided above the excavated section. When the driving axle is slipped into the axle hole, the inner side of the bridge-like member is elastically expanded outwardly by abutment and pressing of a driving surface on the driving axle, so that a reaction force is generated to forcedly press the driving surface. The driving axle bush is driven by the driving axle to move the set of bristles to rotate rightwards and leftwards repeatedly.

3 Claims, 6 Drawing Sheets

BLOCK HEAD STRUCTURE OF ELECTRIC TOOTHBRUSH

BACKGROUND OF THE INVENTION

1. Field of the Invention

The present invention is related to a block head structure of an electric toothbrush; and especially to such a block head structure of an electric toothbrush of which the block head can be changed, so that the block head with such an improved structure can be slipped over and connected to a driving end on the block handle of an electric toothbrush of different style.

2. Description of the Prior Art

An electric toothbrush is a tool for cleaning tooth filth by repeated vibrating to and fro of the bristles moved by an electric motor. By virtue that the bristles of the electric toothbrush is moved by the electric motor, and that the rotation speed of the motor and the vibrating frequencies of the bristles are steady, the tooth filth in the gaps of the teeth can be thoroughly cleared. In comparison with a conventional toothbrush, an electric toothbrush has the advantages of saving more time and effort in brushing teeth; therefore, more and more people use electric toothbrushes in the recent years.

Electric toothbrushes sold in the markets often each includes a block handle and a plurality of block heads, so that a block head on the block handle can be changed in use. In this way, a consumer needs only to buy a more expensive block handle suiting a plurality of block heads for use of all his family members. And when the bristles on a block head is curved and deformed due to long period using, he needs only to buy a new block head instead, and there is no necessity to change for a whole new set of electric toothbrush. This more meets economic efficiency.

The block head structure of an electric toothbrush of the present invention aims at an improvement on the conventional electric toothbrush with a changeable block head structure in order that a single structure can suit block handles of various brands of different manufacturers.

As shown in FIG. 1, a conventional electric toothbrush is comprised mainly of a block handle 10 and a block head 20.

Wherein the block handle 10 is provided for holding by a user, and is provided therein with a storage battery and a motor (not shown); it has a driving end 11 on the front end thereof, the driving end 11 has a driving axle 12 extending therefrom forwardly. When the user presses down a push button on the block handle 10, a motor can be activated to drive the driving axle 12 to rotate for 360 degrees or rotate rightwards and leftwards repeatedly.

The block head 20 is provided with a set of bristles 22 on the front end of a block head sleeve 21, and with a connecting portion 23 on the rear end of the block head sleeve 21. When the connecting portion 23 is slipped over and connected to the driving end 11 on the block handle 10 of the electric toothbrush, the driving axle 12 can drive the set of bristles 22 on the front end of the block head sleeve 21 for rotating rightwards and leftwards repeatedly.

It shall be explained here that, electric toothbrushes sold in the markets are divided into two kinds by the style of motion transmitting. The first kind allows the motor in the block handle 10 to directly drive the driving axle 12 for 360 degree rotation; when the block head 20 is driven, a means in the block head sleeve 21 converts the 360 degree rotating motion into repeated rightward and leftward rotating, thereby, the set of bristles 22 rotates rightwards and leftwards repeatedly. The second kind has the block handle 10 provided therein with a mechanical transmitting mechanism, in order that the driving axle 12 on the front end can rotate rightwards and leftwards repeatedly; thereby, the block head sleeve 21 of the block head 20 is driven to rotate rightwards and leftwards repeatedly; there is no complicated means required therein to change the mode of transmitting.

The above stated two kinds of conventional techniques both have their merits and demerits; while the present invention is an improvement upon the block head 20 of the second kind of conventional electric toothbrush. That is, the structure of the present invention can only be slipped over a conventional block handle 10 of which the driving axle 12 is operated in the way of rotating rightwards and leftwards repeatedly. The interior structure of the block head 20 of the conventional electric toothbrushes is as shown in FIG. 2:

Wherein a driving axle bush 30 is provided between the set of bristles 22 on the front end of the block head sleeve 21 and the connecting portion 23; when the connecting portion 23 is slipped over and connected to the driving end 11 on the block handle 10, the driving axle 12 can be inserted exactly in the driving axle bush 30 to engage therewith axially and radially, thereby, the driving axle 12 can rotate rightwards and leftwards repeatedly, and the driving axle bush 30 also can rotate rightwards and leftwards repeatedly to thereby drive the set of bristles 22.

Referring simultaneously to FIGS. 1 and 2, by the fact that the driving axle 12 and the driving axle bush 30 can only make motion transmission when they are engage with each other axially and radially, the driving axle 12 shall at least be provided with a driving surface 13 and an engaging recess 14. While the driving axle bush 30 is provided for inserting and engagement of the driving axle 12; therefore, the axle hole of the driving axle 12 is in the shape in corresponding to that of the driving surface 13 in order to be provided with a stop block 31. By mutual abutting of the stop block 31 and the driving surface 13 against each other, the two members are radially positioned; when the driving axle 12 is rotated rightwards and leftwards repeatedly, it moves the driving axle bush 30 to rotate rightwards and leftwards repeatedly therewith. And the driving axle bush 30 is provided with an elastic hook 32, when the driving axle 12 is inserted into the driving axle bush 30 to its proper position, the elastic hook 32 engages the engaging recess 14, so that the driving axle 12 and the driving axle bush 30 are axially positioned to further prevent the driving axle bush 30 from axial sliding when it is driven by the driving axle 12 to rotate rightwards and leftwards repeatedly.

The axial and radial engaging and positioning means for the above stated conventional driving axle 12 and the driving axle bush 30 are different in locations and designing depending on different manufacturers. For example, the U.S. Pat. No. 5,289,604 granted to Braun Aktiengesellschaft is a patent with the same device as shown in FIGS. 1 and 2; a conventional driving axle 12 disclosed in FIGS. 3 and 4 has its driving surface 13 and engaging recess 14 different from those of FIGS. 1 and 2, correspondingly, the driving axle bush 30 thereof must be differently designed for transmitting (this is a known technique, and will not be further stated in details). Additionally, those have similar structures include U.S. Pat. Nos. 5,054,149; 4,989,287; 4,827,552; 4,827,550 and 4,291,547 etc. The related structures disclosed in them are based on the same principle as shown in FIGS. 1–4. The present invention provides improvement on the conventional techniques that needs two related means for simultaneous axial and radial positioning and that may have positioning means different in locations and designing depending on different manufacturers.

SUMMARY OF THE INVENTION

In particular, the block head structure of an electric toothbrush of the present invention includes: a block head sleeve, a set of bristles, a driving axle bush and a connecting portion; wherein the driving axle bush is provided on the rear end thereof with an axle hole extending forwardly, the axle hole can be slipped over a driving axle on the driving end of a block handle of the toothbrush. The present invention is characterized in that: the driving axle bush has an excavated section a the area in corresponding to the position of a driving surface of the driving axle; bridge-like member is provided above the excavated section, the front and the rear ends of the bridge-like member are connected with the driving axle bush proper, the top surface of the member is nearby the axle hole. The radial amplitude of the axle hole where the bridge-like member locates is smaller than the radius of the driving axle where the driving surface is; thereby, when the driving axle is slipped into the axle hole, the top surface of the bridge-like member is elastically expanded outwardly by abutment and pressing of the driving surface, hence a reaction force is generated to forcedly press the driving surface. Thereby, the driving axle and the driving axle bush are positioned simultaneously axially and radially to render the driving axle bush to be moved by the driving axle to rotate rightwards and leftwards repeatedly. In this way, the block head structure is improved and can be slipped over a driving end of a block handle of any of various electric toothbrushes, and this is the primary object of the present invention.

The present invention will be apparent in its structural features and effects after reading the detailed description of the preferred embodiment thereof in reference to the accompanying drawings.

DETAILED DESCRIPTION OF THE PREFERRED EMBODIMENT

Figure 5:
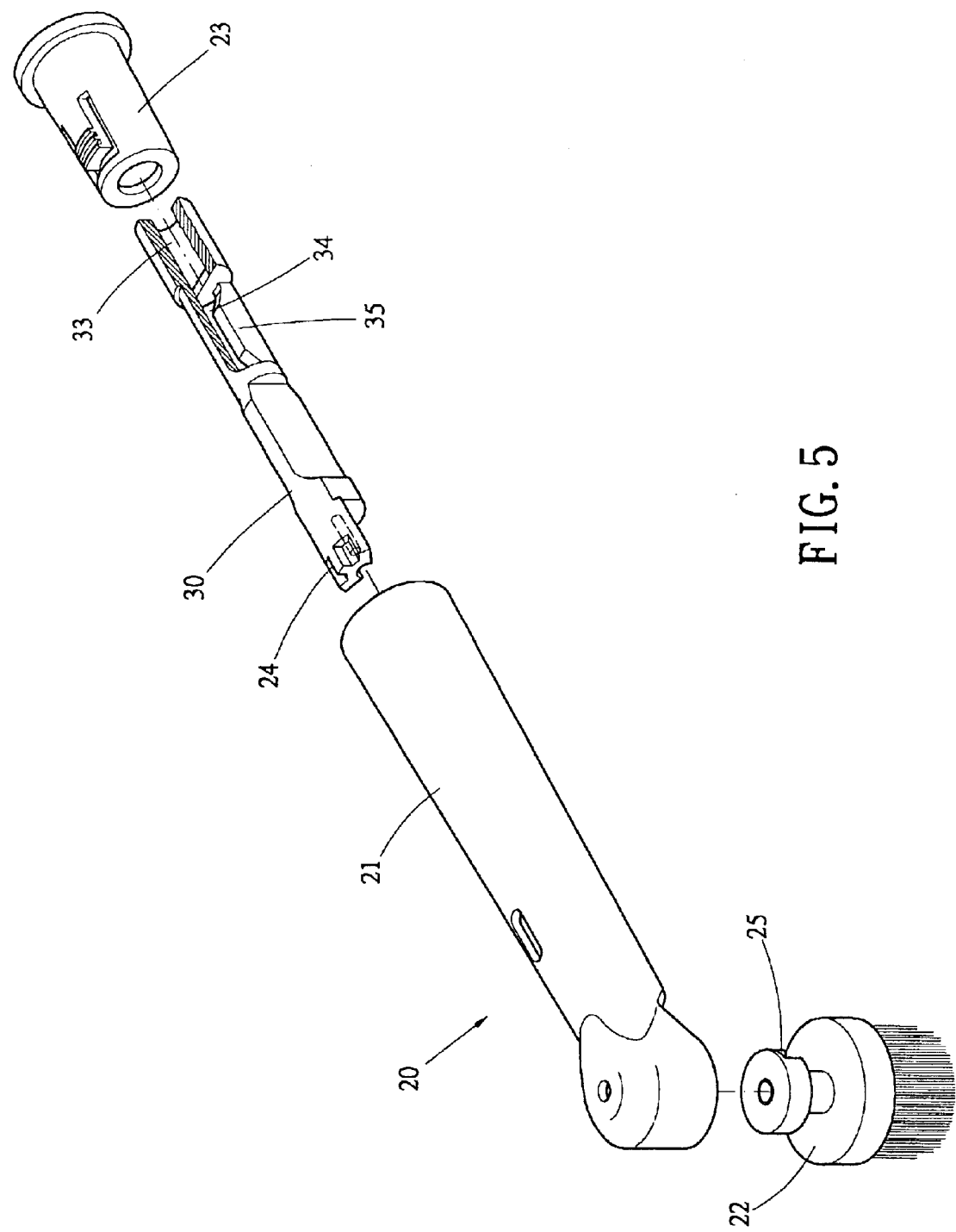
FIG. 5 is an anatomic perspective view of a block head of the present invention, with a driving axle bush thereof in a cut mode.
Figure 6:
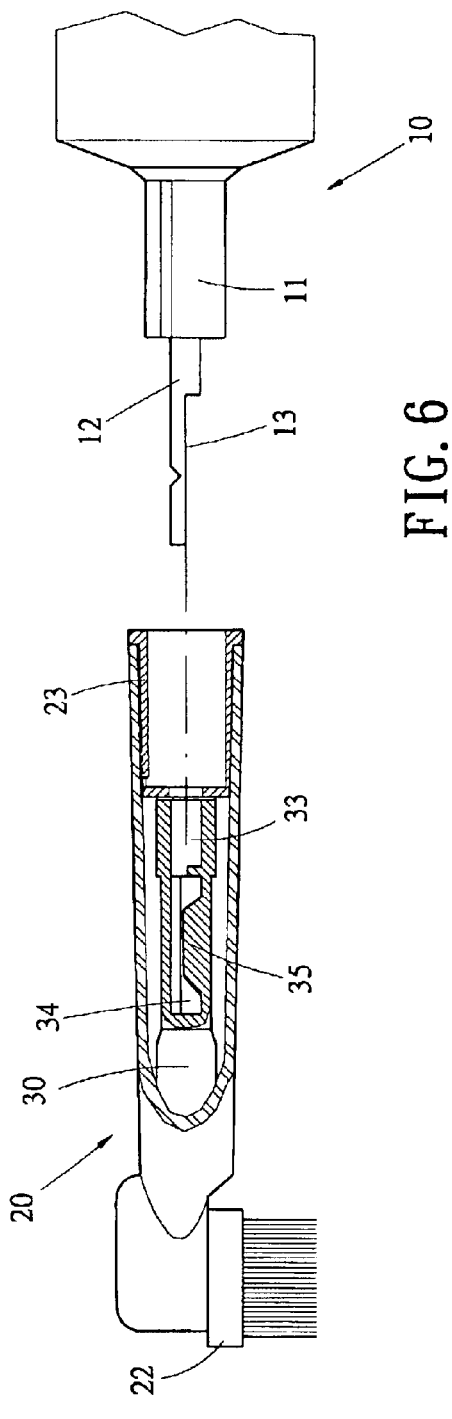
FIG. 6 is a perspective schematic view showing the block handle with the block head of the present invention before assembling.
Figure 7:
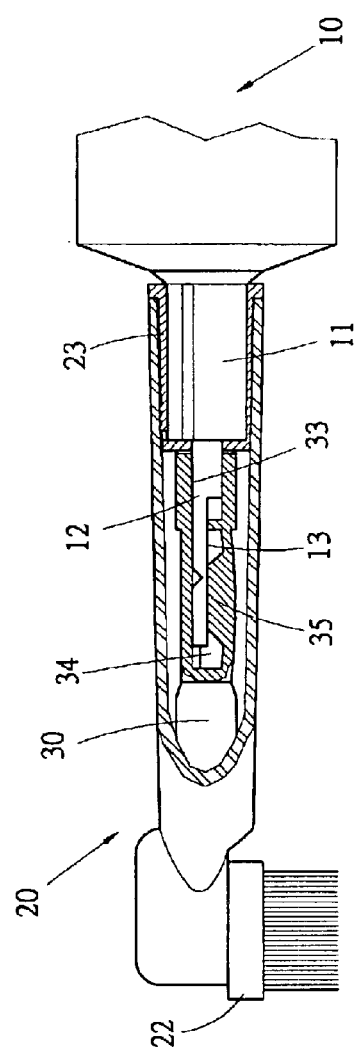
FIG. 7 is a perspective schematic view showing the block handle with the block head of the present invention after assembling.

Referring firstly to FIGS. 5–7, the block head structure of an electric toothbrush of the present invention is comprised of: a block head sleeve 21, a set of bristles 22, a connecting portion 23 and a driving axle bush 30; wherein the block head sleeve 21 is a hollow pipe, and is provided with the set of bristles 22 on the front end thereof, and with the connecting portion 23 on the rear end thereof. The driving axle bush 30 is provided in the front end of the block head sleeve 21 and between the set of bristles 22 and the connecting portion 23; the driving axle bush 30 and the set of bristles 22 are provided on the areas in opposition to each other respectively with gear teeth 24 and 25 which engage with each other. When the driving axle bush 30 rotates rightwards and leftwards, the set of bristles 22 rotates rightwards and leftwards too.

When a block head 20 is connected with the block handle 10 of the electric toothbrush, the connecting portion 23 is slipped over and connected with a driving end 11 of the block handle 10, and a driving axle 12 is inserted and exactly engaged in the axle hole 33 of the driving axle bush 30, thereby, when the driving axle 12 is rotated rightwards and leftwards repeatedly, the driving axle bush 30 is rotated repeatedly rightwards and leftwards repeatedly too to thereby simultaneously rotate the set of bristles 22 by mutual engagement of the gear teeth 24 and 25. The present invention is characterized in that:

The driving axle bush 30 has an excavated section 34 to receive a driving surface 13 of the driving axle 12 after assembling the driving axle bush 30 with the block handle 10; a bridge-like member 35 is provided above the excavated section 34, the front and the rear ends of the bridge-like member 35 are connected with the driving axle bush 30 proper, the top surface of the member 35 is nearby the axle hole 33. The radial amplitude of the axle hole 33 where the bridge-like member locates is smaller than the radius of the driving axle 12 where the driving surface 13 is.

When the driving axle 12 is slipped into the axle hole 33, the top surface of the bridge-like member 35 is nearby the axle hole 33, the radial amplitude of the axle hole 33 here is smaller than the radius of the driving axle 12, thereby the top surface of the bridge-like member 35 is elastically expanded outwardly by abutment and pressing of the driving surface 13; meantime, the front and the rear ends of the bridge-like member 35 are connected with the driving axle bush 30 proper and a above the excavated section 34 to leave space for displacement. Thereby, when the bridge-like member 35 is abutted and pressed by the driving surface 13 of the driving axle 12, it will be deformed to expand outwardly, hence a reaction force is generate to forcedly press the driving surface 13 with its top surface.

When the bridge-like member 35 generates the reaction force to forcedly press the driving surface 13, by mutual abutting of the too surface of the bridge-like member 35 on the driving surface 13 of the driving axle 12, the two members are radially positioned; when the driving axle 12 is rotated rightwards and leftwards, it moves the driving axle bush 30 to rotate rightwards and leftwards therewith through the bridge-like member 35. And by the fact that the bridge-like member 35 generates the reaction force to forcedly press the driving surface 13, a friction force is generated between the driving surface 13 and the top surface of the bridge-like member 35, so that the bridge-like member 35 clamps tight the driving axle 12 to further make axial positioning of the driving axle bush 30 and the driving axle 12 to avoid separating and falling off of the driving axle bush 30 and the block head 20 when the driving axle 12 rotates rightwards and leftwards repeatedly. Certainly, if a user exerts on the block head 20 a forward pulling force larger than the friction force generated between the driving surface 13 and the top surface of the bridge-like member 35, the block head 20 can be detached from the block handle 10 to change it for another block head 20.

Figure 1:
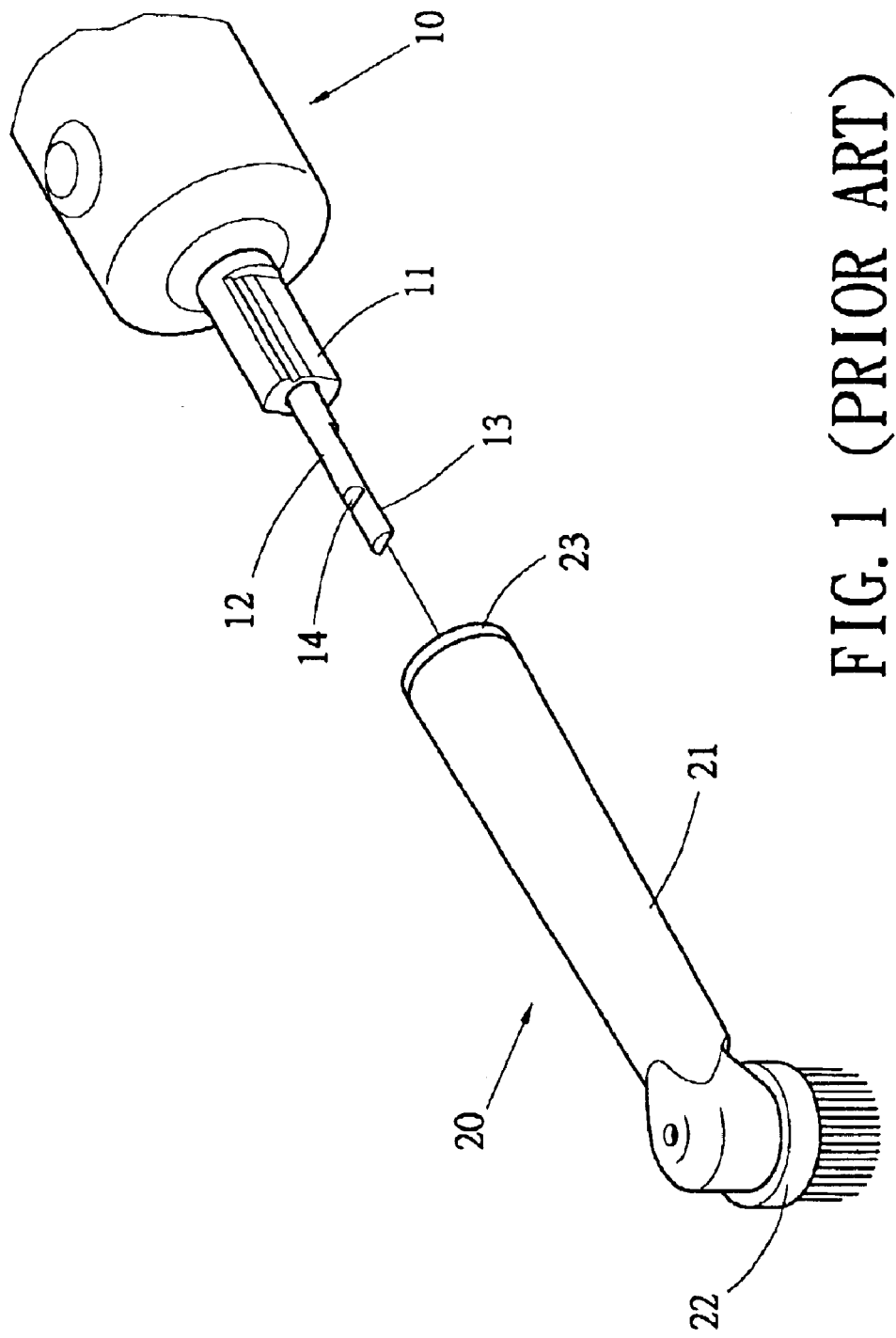
FIG. 1 is an anatomic perspective view of a block handle and a block head of a conventional electric toothbrush.
Figure 2:
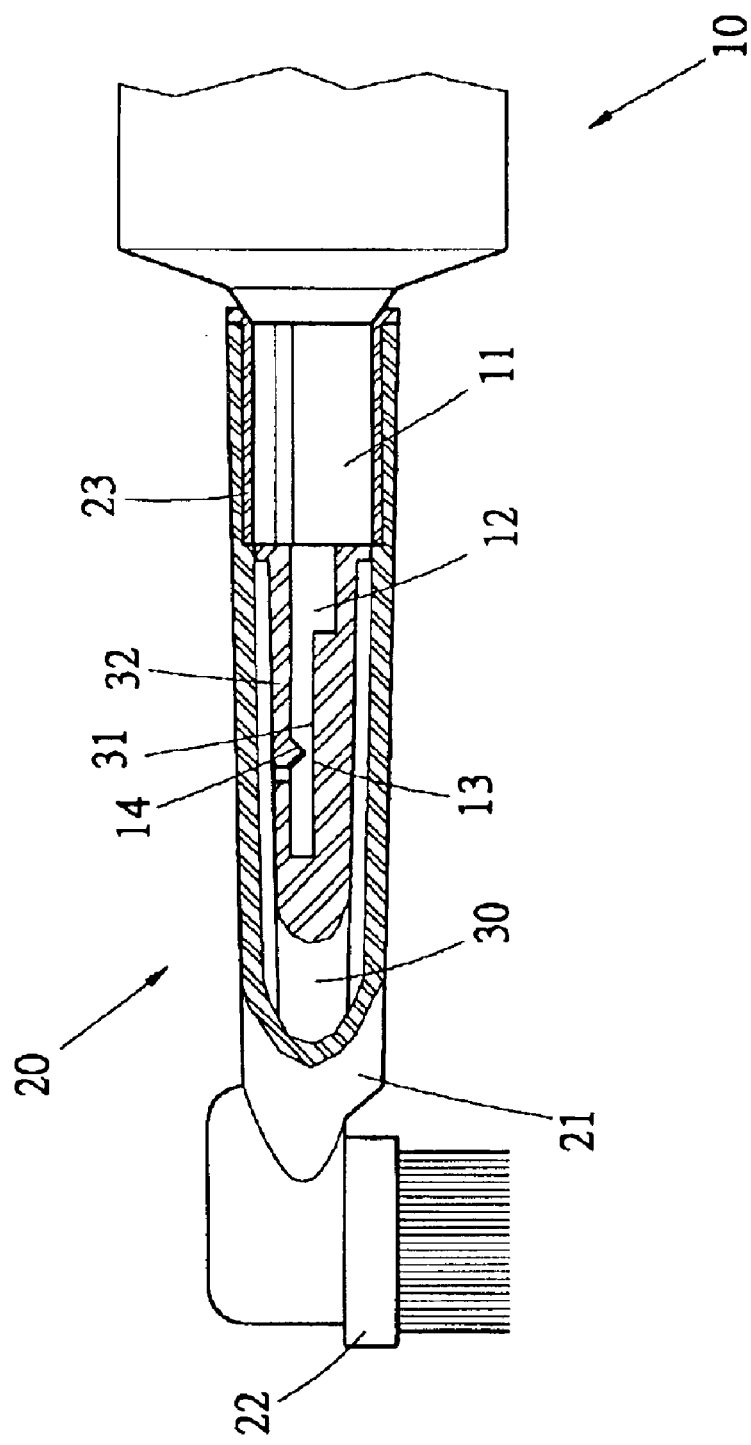
FIG. 2 is a sectional schematic view showing assembling of a conventional block handle with a block head of the conventional electric toothbrush.
Figure 3:
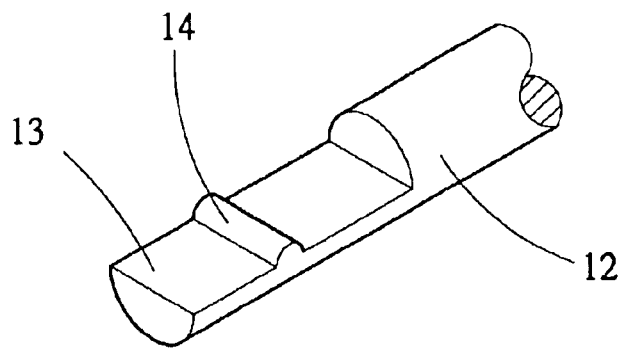
FIGS. 3 and 4 are perspective views of two kinds of driving axles of other two conventional electric toothbrushes.
Figure 4:
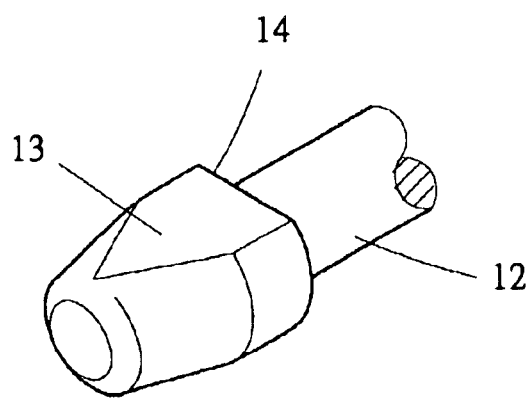

With the above stated structure, the block head structure of an electric toothbrush of the present invention makes tight abutment of the driving axle 12 again t the bridge-like member 35 of the driving axle bush 30 to effect axial and radial positioning simultaneously; there is no necessity to use the mechanism that a conventional driving axle bush must be provided to be similar to the providing of the driving surface 13 and an engaging recess 14 thereof (referring to FIG. 2), 50 so that the block head can be connected with a block handle of any of various electric toothbrushes to achieve the primary object of the present invention.

Moreover, by virtue that when the driving axle 12 and the driving axle bush 30 are rotated rightwards and leftwards repeatedly, the bridge-like member 35 is a force bearing area, thereby, when in practice of the present invention, the driving axle bush 30 and the bridge-like member 35 are preferably integrally formed of the material fiberglass reinforced plastic to increase their strength and life of use. The inventor of the present invention has successfully made a sample being proved workable after a long period test, and is ready to provide this sample when is required for the present application.

Figure 8:
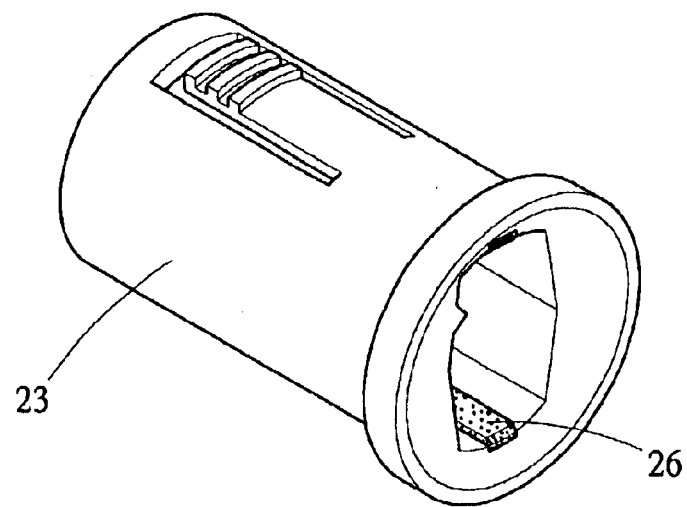
FIG. 8 is a perspective view of an embodiment of a connecting portion of the block head of the present invention.

Further please reference to FIG. 8, in practicing the present invention, the connecting portion 23 is provided on the inner side thereof with a slide-proof block 26 which is preferably made of rubber or applied with rubber. When the connecting portion 23 is slipped over the driving end 11 on the block handle 10 of the electric toothbrush (referring to FIG. 7), the slide-proof block 26 can increase the friction force between the connecting portion 23 and the driving end 11, thereby, axial positioning by means of the friction force between the above stated driving surface 13 and top surface of the bridge-like member 35 can be strengthened, and the block head 20 will be uneasy to drop.

The names of the members composing the present invention shown in the drawings are only for illustrating a preferred embodiment of the present invention, and not for giving any limitation to the scope of the present invention. It will be apparent to those skilled in this art that various equivalent modifications or changes can be made to the elements of the present invention without departing from the spirit of this invention. Accordingly, all such modifications and changes also fall within the scope of the appended claims of this invention.

What is claimed is:

1. A block head structure of an electric toothbrush comprising:

a block head sleeve, a set of bristles, a connecting portion and a driving axle bush, wherein said block head sleeve is provided with said set of bristles on the front end thereof, and with said connecting portion on the rear end thereof; said driving axle bush is provided in said block head sleeve and between said set of bristles and said connecting portion; when said block head is connected with a block handle, said connecting portion is slipped over and connected to a driving end on said block handle, a driving axle thus is inserted and engaged in an axle hole of said driving axle bush, thereby, when said driving axle is rotated rightwards and leftwards repeatedly, said driving axle bush and said set of bristles are rotated simultaneously; said block head structure is characterized in that:

said driving axle bush has an excavated section to receive a driving surface of said driving axle after assembling said driving axle bush with said block handle; a bridge-like member is provide above said excavated section, the front and the rear ends of said bridge-like member are connected with said driving axle bush, the top surface of said bridge-like member is nearby said axle hole; the radial amplitude of said axle hole where said bridge-like member locates is smaller than the radius of said driving axle where said driving surface is; thereby when said driving axle is slipped into said axle hole, said top surface of said bridge-like member is elastically expanded outwardly by abutment and pressing of said driving surface, hence a reaction force is generated to forcedly press said driving surface with said top surface; thereby, said driving axle and said driving axle bush are positioned simultaneously axially and radially, so that when said driving, axle is rotated rightwards and leftwards repeatedly, said driving axle bush and said set of bristles are rotated simultaneously.

2. The block head structure of an electric toothbrush as in claim 1, wherein said driving axle bush and said bridge-like member are integrally formed of a fiberglass reinforced plastic material.

3. The block head structure of an electric toothbrush as in claim 1, wherein said connecting portion is provided on the inner side thereof with slide-proof block.

* * * * *